United States Patent [19]

Ogino

[11] Patent Number: 5,560,889
[45] Date of Patent: Oct. 1, 1996

[54] SAMPLE TREATMENT APPARATUS

[75] Inventor: Shinichi Ogino, Kobe, Japan

[73] Assignee: Toa Medical Electronics Co., Ltd., Hyogo-ken, Japan

[21] Appl. No.: 436,561

[22] Filed: May 8, 1995

[30] Foreign Application Priority Data

May 9, 1994 [JP] Japan .................... 6-095207

[51] Int. Cl.⁶ .................................. G01N 1/18
[52] U.S. Cl. ............... 422/82.05; 422/110; 436/178; 356/39; 356/72; 356/73
[58] Field of Search .................. 356/39, 72, 73; 73/61.72; 422/68.1, 82.01, 82.05, 110; 436/63, 178, 179

[56] References Cited

U.S. PATENT DOCUMENTS

| | | | |
|---|---|---|---|
| 3,900,290 | 8/1975 | Hornstra | 73/64.1 |
| 4,066,359 | 1/1978 | Bucalo | 356/36 |
| 4,395,493 | 7/1983 | Zahniser et al. | 435/289 |
| 5,266,495 | 11/1993 | Lapidus | 436/63 |

FOREIGN PATENT DOCUMENTS

| | | |
|---|---|---|
| 59-183813 | 10/1984 | Japan . |
| 60-186757 | 9/1985 | Japan . |
| 5-252996 | 10/1993 | Japan . |
| 5-273217 | 10/1993 | Japan . |

*Primary Examiner*—Jeffrey Snay

[57] ABSTRACT

A sample treatment apparatus includes a sample sucking section, a sample concentration detecting section, and a sample condensing section. The sample concentration detecting section detects a change of the quantity of light emitted from a light source by a light receiving element to measure the quantity of light absorbed or scattered by the particle component in a sample. The signal detected by the light receiving element is processed by a sample concentration controller and the approximate particle concentration of the sample is obtained. The sample condensing section is provided with a syringe and a filter unit, and the sample to be transferred from a chamber to the syringe is condensed in the filter unit.

13 Claims, 5 Drawing Sheets

SAMPLE TREATMENT APPARATUS

BACKGROUND OF THE INVENTION

1. Field of the Invention

The present invention relates to a sample treatment apparatus, particularly to a sample treatment apparatus for applying a predetermined treatment to a liquid sample containing a particle component.

2. Description of the Prior Art

To measure sizes of and the number of particulates, microorganisms, or organic cells, sample measurement apparatuses have been used so far which use the "electrical-resistance-type particle measuring method", "sedimentation-type particle measuring method", and "light-scattering diffraction-type particle measuring method".

These apparatuses are marked with, for example, "For the particle concentration of 1,000 particles/µl or more: measurement reproducibility (random error) of 10% or less" in order to assure the measurement precision (reproducibility or accuracy). It is generally accepted that measurement precision decreases (measurement reproducibility value increases) as the particle concentration decreases.

Therefore, to improve the measurement precision for a liquid sample with a low particle concentration, the following methods are used.

(i) To increase the number of particles to be measured by extending the measuring time.

(ii) To raise the particle concentration by previously centrifuging a sample to be measured and removing the supernatant liquid.

In the case of a sample measuring apparatus using the method of "extending the measuring time" in Item (i), for example, the extensible measuring time is set to a value of 2 to 3 times larger than the standard measuring time. That is, the extension of the measuring time is limited. In addition, when the concentration of particles to be measured is low, a preferable result is rarely obtained even if the measuring time is extended.

In the case of a particle analyzer such as a flow cytometer, for example, the measuring time is approx. 10 sec because of the limitations of the apparatus, and thereby the measurable amount of a sample is limited to 2 to 3 µl. Therefore, as for a sample with a particle concentration of approx. 1,000 particles/µl, a stable result is obtained because the reproducibility (random error) comes to approx. 2%. As for a sample with a particle concentration of approx. 100 particles/µl, however, inconsistent results are obtained because the measurement reproducibility comes to approx. 6%. Even if the measuring time is increased threefold, the reproducibility is improved only up to approx. 3%.

To measure the above sample at a reproducibility (random error) of approx. 2%, it is necessary to increase the measuring time 10 to 15 times or increase the sample concentration 10 to 15 times. However, because it is generally difficult to increase the measuring time tenfold, the measuring time has been increased only several times.

Therefore, a method of "measuring a sample once and thereafter measuring it again by setting a proper measuring time" is considered. However, this method has the disadvantage that measurement must be performed twice and therefore the operation is impractical.

Moreover, the method of "previously centrifuging a sample to be measured" in Item (ii) has the disadvantage that measurement must be performed at least twice paralleling the process of "preliminary measurement→treatment before actual measurement (e.g. centrifugal separation)→actual measurement" and therefore the operation is considered to be impractical. Furthermore, the method has the disadvantage that a sample cannot be accurately analyzed when the amount of the sample is too small.

Recently, the necessity for measuring a sample of very small amount has been increased. In addition, in the case of a sample measuring apparatus such as a flow cytometer, though a sample of several hundred microliters is necessary, the actual amount of the sample to be measured is only several microliters, and therefore the bulk of the sample is wasted.

The present invention, "the Sample Treatment Apparatus", is designed to solve the above problems and its objective is to provide a sample treatment apparatus making it possible to execute a high measurement precision for a liquid sample of small amount without extending the measuring time or requiring any special pre-treatment.

SUMMARY OF THE INVENTION

The present invention provides a novel sample treatment apparatus comprising a concentration measurement means for measuring the concentration of an object particle component contained in a liquid sample; a concentration adjustment unit for adjusting the concentration of the particle component of the sample to a predetermined value, which is connected to the concentration measurement means and provided with a front chamber having an intake port and a discharge port of the sample, a rear chamber having a discharge port of the liquid component of the sample, and a filter set so as to separate both chambers from each other and capable of passing the liquid component of the sample without passing the particle component of the sample; a liquid discharge means connected to the rear chamber of the unit to discharge the liquid component from the rear chamber and the sample from the front chamber; and a control means for operating the liquid discharge means and controlling the concentration of the sample in accordance with the measured results by the concentration measurement means.

Hitherto, a sample had to be remeasured by adjusting the concentration of the sample by another apparatus after preliminary measurement of the sample. However, the sample treatment apparatus of the present invention creates the economy of time and labor because the measurement can be performed with single measurement by adjusting the sample to a proper concentration.

Furthermore, it is possible to assure accurate measurement results even for a low-concentration sample where measurement accuracy was previously impossible.

In addition, it is possible to detect a cell or particle which has a low appearance frequency and couldn't produce prior measurable results.

Finally, it is possible to condense a sample up to a sample capacity (almost the same capacity as the capacity used by a measuring system) which couldn't have been realized by the prior techniques. However the current invention allows the sample to be condensed in a channel by using the filter of a concentration adjustment unit.

DESCRIPTION OF THE PREFERRED EMBODIMENTS

Figure 1:
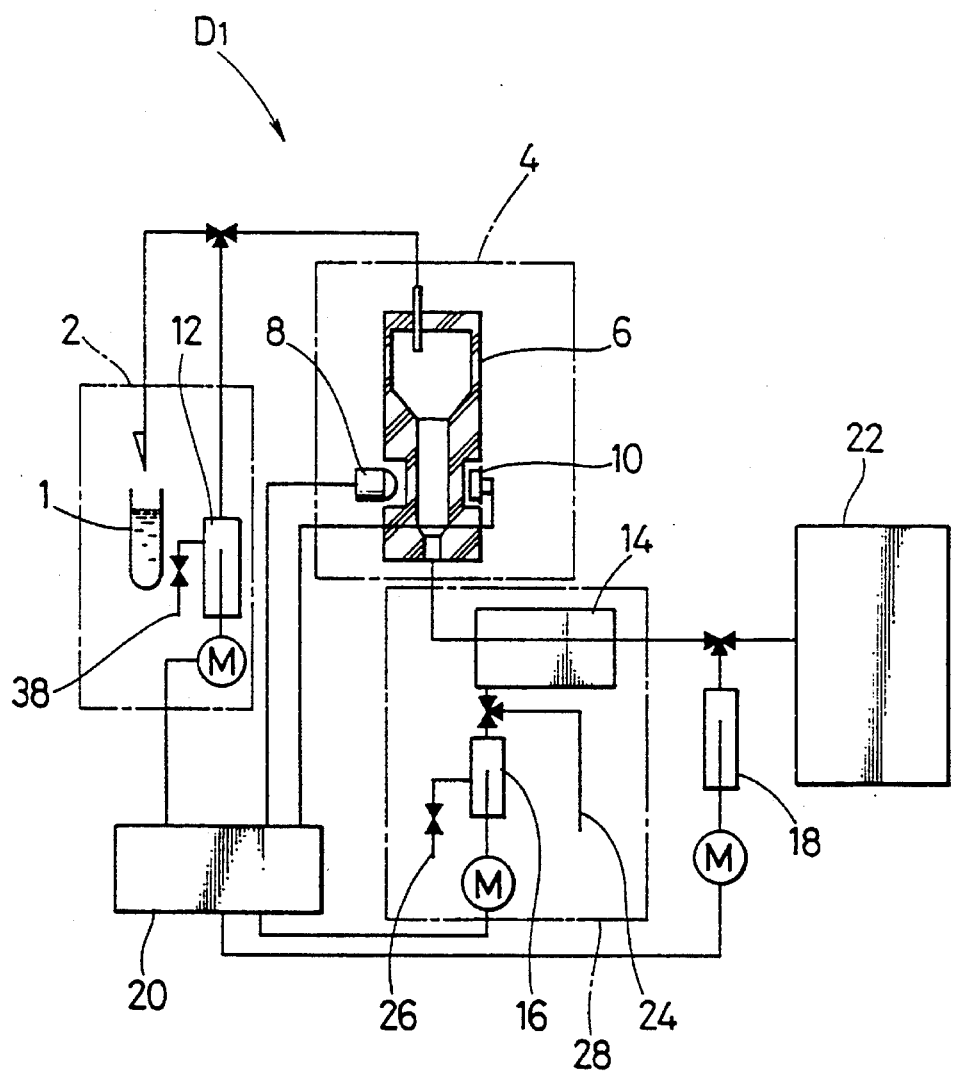
FIG. 1 is a block diagram showing a basic diagram of a sample treatment apparatus according to an embodiment 1 of the present invention.

As for the liquid sample, a sample containing particle components such as particulates, microorganisms, organic cells or the like may be used. Examples of the liquid samples include humor such as blood, lymph or urine. For such humor, the type of, and the number of, organic particle cells such as erythrocytes or leukocytes contained in the humor can be analyzed.

The concentration measurement means measures the concentration of particle component contained in the sample. The concentration measurement means, for example, comprises a chamber for storing a sample to be measured, a light source, and a light receiving element, and obtains the particle concentration of the sample by detecting the quantity of light emitted from the light source and passing through the sample and measuring the amount of light absorbed or scattered by particle components in the sample.

The concentration adjustment unit adjusts object particle components in a liquid sample to a predetermined concentration; for example, when measuring the size of and the number of the particle component such as particulates, microorganisms, or organic cells in the liquid sample by a particle measuring apparatus, the unit adjusts the object particle component to a concentration most suitable for the measurement. The concentration adjustment unit has a front chamber, a rear chamber, and a filter. The front chamber has an intake port and a discharge port for the sample. The rear chamber has a discharge port for the liquid component in the sample. The filter allows the liquid component of the sample to flow through, but prevents the object particle component in the sample from permeating.

This type of the concentration adjustment unit is mainly used to condense a liquid sample (condensation unit). However, when the concentration of the particle component measured by the concentration measurement means is higher than the predetermined concentration as it will be mentioned later, the unit is used for diluting the liquid sample. When the concentration of the particle component is equal to the predetermined concentration, the unit is used for transferring the liquid sample directly to its destination without condensing or diluting the liquid sample.

When the concentration adjustment unit is used as a condensation unit, the unit captures particle component in the liquid sample by filtering the sample with a filter and as a result, condenses the sample. The condensation unit has a front chamber for taking in the sample, a rear chamber for discharging the liquid component in the sample. A filter is provided so as to separate the front chamber from the rear chamber and for collecting the particle component in the sample. The front cheer of the condensation unit has an intake port and a discharge port. The rear cheer has a discharge port for the liquid component in the sample, and the filter allows the liquid component in the sample to flow through without passing the object particle component in the sample. The inflow and outflow of the sample to and from the front chamber and the discharge of the liquid component from the rear chamber is performed through the employment, for example, of a syringe.

The liquid discharge means is connected to the rear chamber of the concentration adjustment unit to discharge liquid component from the rear cheer and the sample from the front chamber. When the concentration adjustment unit serves as the condensation unit, the liquid discharge means is connected to the rear chamber of the condensation unit to discharge the liquid component from the sample. Then, the liquid discharge means contributes to condense the sample together with the condensation unit. The liquid discharge means is provided with, for example, a syringe and a selector valve.

The control means regulates the liquid discharge means in accordance with the measured results by the concentration measurement means. That is, the control means determines the amount of liquid to be discharged from the liquid discharge means in accordance with the condensation rate or the particle concentration value obtained by the concentration measurement means and indicates the operation of the liquid discharge means.

It is preferable that the sample treatment apparatus of the present invention is further provided with the means of a liquid feed. The liquid feed means is connected to the concentration adjustment unit for example, the rear chamber of a condensation unit to feed a liquid such as dilute liquid, or cleaning liquid to the filter. The liquid feed means is provided with, for example, a syringe and a selector valve, when the sample treatment apparatus of the present invention is further provided with the means of a liquid feed, the control means regulates the liquid discharge means and also systematizes the concentration measurement means and the liquid feed means. The liquid discharge means (the liquid feed means) can be used as the liquid feed means (the liquid discharge means).

It is preferable that the sample treatment apparatus of the present invention is further provided with a dye feed means for feeding a dye to be added to a sample in addition to the liquid feed means, for example, by being connected to the chamber of the concentration measurement means. The dye feed means performs desired analysis by coloring a specific cell or the like in the sample with a predetermined dye and measuring the fluorescence emitted from the dye. The dye feed means is provided with, for example, a syringe and a selector valve. It is unnecessary to dye a sample by the means built in the sample treatment apparatus of the present invention as its component unit.

It is preferable that, in the sample treatment apparatus of the present invention, the condensation unit is further provided with a feed channel connected to the front chamber of the unit to feed a condensed sample to an analyzing system. In this case, the sample treatment apparatus of the present invention is used by being built in or connected to a particle analyzer such as a flow cytometer as an analyzing system.

Four embodiments of the present invention are described below in detail by referring to the accompanying drawings. However, the present invention is not restricted to these embodiments.

Embodiment 1

FIG. 1 illustrates the embodiment 1 of the present invention. In FIG. 1, a sample treatment apparatus $D_1$ is provided with a sample sucking section 2, a sample concentration detecting section 4 serving as a concentration measurement means, and a sample condensing section 28. The sample sucking section 2 is a section for drawing a liquid sample (blood) to be measured and stored in sample vessel 1. The sample sucking section 2 has a sample sucking syringe 12. The sample sucking syringe 12 is controlled by a sample concentration controller 20, which serves as a control means. The sample of a certain amount determined by the syringe 12, is led to the sample concentration detecting section 4.

The sample concentration detecting section 4, is provided with a sample concentration detecting chamber 6, a light source 8, and a light receiving element 10. The sample concentration detecting section 4, measures the amount of light absorbed or scattered by particle components in a sample by detecting the variation of the amount of light radiated from the light source 8, and passed into the sample in chamber 6, by the light receiving element 10. A signal detected by the light receiving element 10, is processed by the sample concentration controller 20. Hence, an approximate particle concentration of the sample is obtained.

The sample concentration detecting section 4 uses a particle measuring method according to nephelometry as a method for previously measuring the particle concentration in the sample. For example, it is possible to realize a method of "measuring the change of the amount of LED light passing through chamber 6 by using an LED as the light source 8 and a photodiode as the light receiving element 10". Then, the particle concentration is determined by the intensity of the light entered into cheer 6 and that of the transmitted light received by the light receiving element 10 as following.

That is, according to the Lambert-Beer law, when assuming particle concentration per unit volume as C, incident light intensity as $I_t$, transmitted light (outgoing light) intensity as It, and absorption coefficient as $\epsilon$, the relation of them is shown by the following expression.

$$\log I_t = \log I_o - C\epsilon \log 10$$

Therefore, the particle concentration of the sample to be measured is obtained from the following expression by measuring the ratio between incident light and transmitted light.

$$C\epsilon = \log (I_o/I_t)$$

By comparing the measurement data with the particle concentration of the standard sample, the condensation rate of the sample is determined and syringe 12 is operated according to the condensation rate. In this case, it is also possible to set the particle concentration for comparison to a higher value.

Figure 2:
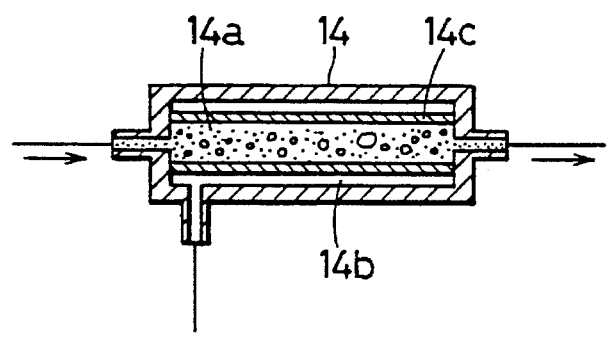
FIG. 2 is a diagram explaining the sample transfer state in a filter unit of the sample treatment apparatus as shown in FIG. 1.

The sample condensing section 28, is provided with a sample condensing syringe 16, serving as a liquid discharge means and a filter unit 14, serving as the condensation unit. The filter unit 14, as shown in FIG. 2, has a front chamber 14a where the sample enters, a rear chamber 14b where the liquid component in the sample exits, and a filter 14c provided so as to separate the front chamber 14a from the rear chamber 14b. The filter 14c uses a hydrophilic hollow fiber filter made of polyethylene or the like in consideration of the chemical resistance. The sample condensing section 28, condenses the sample to be transferred from the chamber 6, to a sample transfer syringe 18, by using the front and rear chambers 14a and 14b and the filter 14c.

The sample concentration controller 20, determines the condensation rate of the sample so that a measuring system performs measurement at the optimum particle concentration in accordance with the particle concentration measured by the sample concentration detecting section 4. Moreover, the sample concentration controller 20, controls the operations of the sample sucking syringe 12, sample condensing syringe 16, and sample transfer syringe 18. The sample condensing syringe 16 sucks the liquid in the filter unit 14 mainly in accordance with the control signal which is produced from the sample concentration controller 20.

Figure 3:
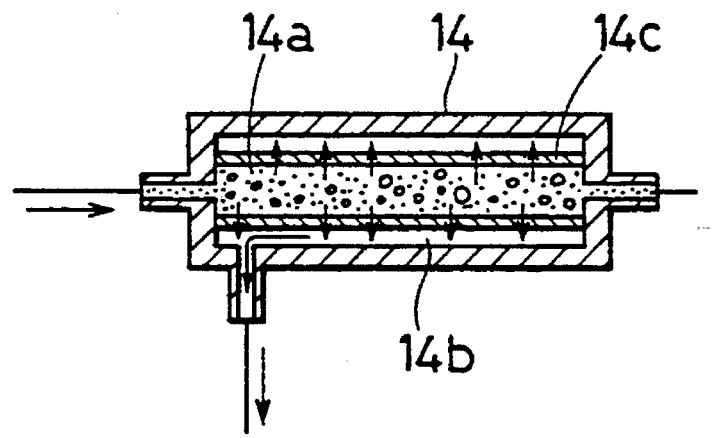
FIG. 3 is a diagram explaining the sample condensation state in the filter unit of the sample treatment apparatus of FIG. 1.

In the sample condensing section 28, as shown in FIG. 3, the liquid component in the sample sent into the front chamber 14a in the filter unit 14, is sucked by the syringe 16, and discharged from a liquid discharge port 26. As a result, only the particle component of the sample remains inside of the filter 14 and the sample is thus condensed.

Hereafter, the description is made in accordance with the measuring procedure.

For example, in the case where making the standard sample concentration as 2,000 particles/µl and measuring two kinds of sample having concentration of 200 particles/µl (sample A) and 4,000 particles/µl (sample B), it is found that the sample A must be condensed 10 times and that sample B can be measured as it is or measured by diluting it two times in order to measure them in the reproducibility (random error) almost equal to that of the standard sample.

[In the case of the measurement of the sample A]

The sample A sucked by the sample sucking section 2 (the sucked amount of the sample A is assumed as 1 ml) is injected into the chamber 6, of the sample concentration detecting section 4 and the transmitted light intensity ($I_tA$) of the sample A is measured under the incident light intensity $I_o$. The measured result is compared with the transmitted light intensity ($I_tS$) of the standard sample in the sample concentration controller 20. In this case, if the transmitted light intensity $I_tA$ of the sample A equals 1.26 $I_tS$, the expression "$C\epsilon = \log (I_tA/I_tS) = \log (1.26\ I_tS/I_tS) = \log 1.26$" is obtained from the above expression "$C\epsilon = \log (I_o/I_t)$". That is, it is found that the particle concentration of the sample A is approx. 1/10 (=log 1.26) of the particle concentration of the standard sample.

The measured sample A is transferred to the filter unit 14, in the sample condensing section 28, by the sample transfer syringe 18 (FIG. 2). In the filter unit 14, the sample condensing syringe 16, operates in accordance with the signal sent from the sample concentration controller 20 and the sample in the filter unit 14 is condensed 10 times by sucking 900 µl of the liquid component (FIG. 3).

Figure 4:
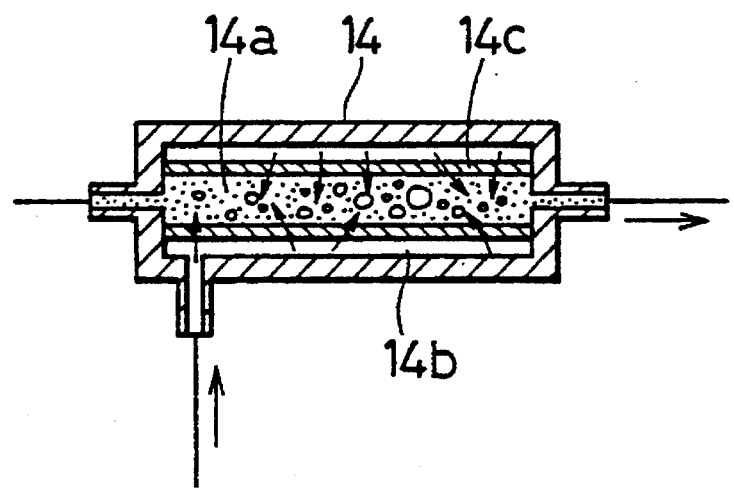
FIG. 4 is a diagram explaining the removal of particle component in a sample of the filter unit of the sample treatment apparatus of FIG. 1.

Thereafter, the particle component attached to the inner surface of the filter 14c is removed by a method of "feeding a very small amount of cleaning liquid from a cleaning liquid (diluent liquid) intake port 24 to the filter unit 14, through syringe 16 (in this case, the syringe 16 functions as liquid feed means)" (FIG. 4). In this case, it is possible to include the operation of agitating and homogenizing the sample in the filter unit 14. Furthermore, it is possible to feed the previously discharged liquid component instead of "feeding the cleaning liquid".

Sample A, condensed to the optimum concentration, (100 μl) is transferred to a particle analyzer 22, as an analyzing system through a feed channel connected with the front chamber 14a of the filter unit 14 (FIG. 2). Then, the cleaning liquid is fed to the particle concentration detecting section 4, from the cleaning liquid intake port 38 through the syringe 12, and cheer 6 is cleaned. Further, the cleaning liquid is transferred to the filter unit 14, and after it cleans the inside of the channel, it is then discharged through the particle analyzer 22.

Moreover, it is possible to remove the particles and bubbles remaining inside the surface of filter 14c of the filter unit 14, by inversely feeding a proper amount of cleaning liquid from the cleaning liquid intake port 24 through syringe 16.

By using the above method, it is possible to remove the liquid component of approx. 900 μl which is remaining after excluding "the volume of the sample volume actually measured by the particle analyzer 22, plus the tube-capacity α" (approx. 100 μl) from the volume of 1 ml of the sample prepared in the cheer 6. Therefore, approx. 10 times the concentration can be made and it is possible to measure even a low-concentration sample with a sample sucking quantity equal to that of the standard sample.

Embodiment 2

Conventionally, in an optical cytoanalyzer such as the flow cytometer, a method which performs the analysis by dyeing specified cells of the sample with a fluorescent dye such as EB (ethidium bromide) or AO (acridine orange) and measuring the fluorescence emitted from the cells is used. For this type of apparatus, the amount of dye to be applied is constant regardless of the sample concentration. That is, an amount of dye corresponding to the volume of a diluted sample prepared in the pretreatment is applied.

However, not all of the amount of applied dye combines with the specified cells but a large quantity of dye not combined with the specified cells remains in the sample. In particular, when the concentration of cells to be dyed is low, ample of dye remains in the sample. As a result, the dye remaining in the diluted sample is observed as background fluorescence at measurement to cause the decrease of the S/N ratio (signal-to-noise ratio) at the measurement.

The residual concentration of dye increases when the number of cells to be dyed is small or the volume of a cell to be dyed is also small. Even in the case where the background noise is small, there is a problem that cells difficult to measure become even more difficult to calibrate.

Therefore, it is the object of this embodiment 2 to remove the extra dye remaining in a pre-treated sample by the method shown below and improve the S/N ratio at measurement by decreasing the background noise of the sample.

Figure 5:
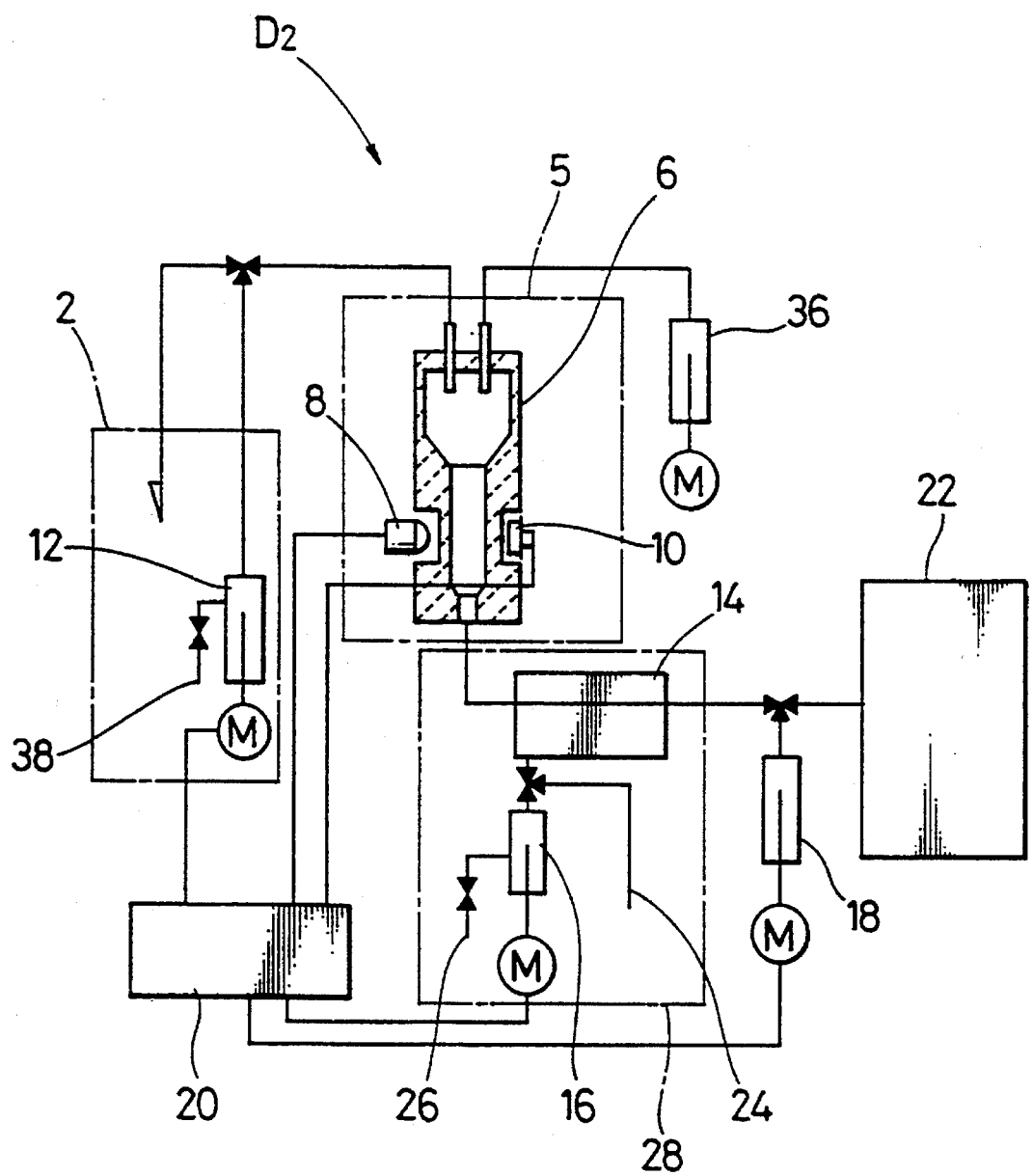
FIG. 5 is a block diagram illustration outlining the basic structure of the sample treatment apparatus according to another embodiment 2 of the present invention.

In FIG. 5 which illustrates the embodiment 2 of the present invention, a sample treatment apparatus $D_2$ is provided with the sample sucking section 2, a sample concentration detecting section 5 serving as the concentration measurement means, and the sample concentrating section 28. The sample extracted by the sample sucking section 2, is injected into the sample concentration detecting section 5 and the transmitted-light quantity is measured. The measured result is compared with the transmitted light quantity of the standard sample by the sample concentration controller 20. Thereby, the particle concentration of the sample is roughly decided. Moreover, a predetermined fluorescent dye such as EB or AO is applied from a coloring solution syringe 36, and serves as a dye feed means and the specified cells of the sample are dyed.

The dyed sample is transferred to the filter unit 14, (condensation unit) in the sample condensing section 28, by the sample transfer syringe 18. The liquid component of the sample dyed by the sample condensing syringe 16, is drawn into filter unit 14 and particle component of the sample remains. The sucked liquid component (liquid component containing extra dyeing solution) is discharged from a liquid discharge port 26, and thereafter the same amount of cleaning liquid is injected into the filter unit 14 from the cleaning liquid (diluent liquid) intake port 24, through syringe 16.

The sample from which the extra dye is removed is led to the particle analyzer 22 such as the flow cytometer by the sample transfer syringe 18. The predetermined measurement is carried out by the particle analyzer 22.

Moreover, in the case of when a sample where it is judged that the sample should be condensed when the sample concentration is detected in chamber 6, dye is removed from the sample by the sample condensing syringe 16 serving as the liquid discharge means and thereafter the diluent liquid is prepared so that the sample has a proper condensation rate and is then injected by the sample concentration controller 20.

As described above, the sample treatment apparatus $D_2$ makes it possible to perform the measurement with a high S/N ratio because background noise due to the extra dye can be decreased by removing the extra dye in the sample and still have the particle component remain.

In the sample treatment apparatus $D_2$, a component of the same symbol as that of the sample treatment apparatus $D_1$ of the embodiment 1 is substantially the same as the component of the sample treatment apparatus $D_1$.

Embodiment 3

Figure 6:
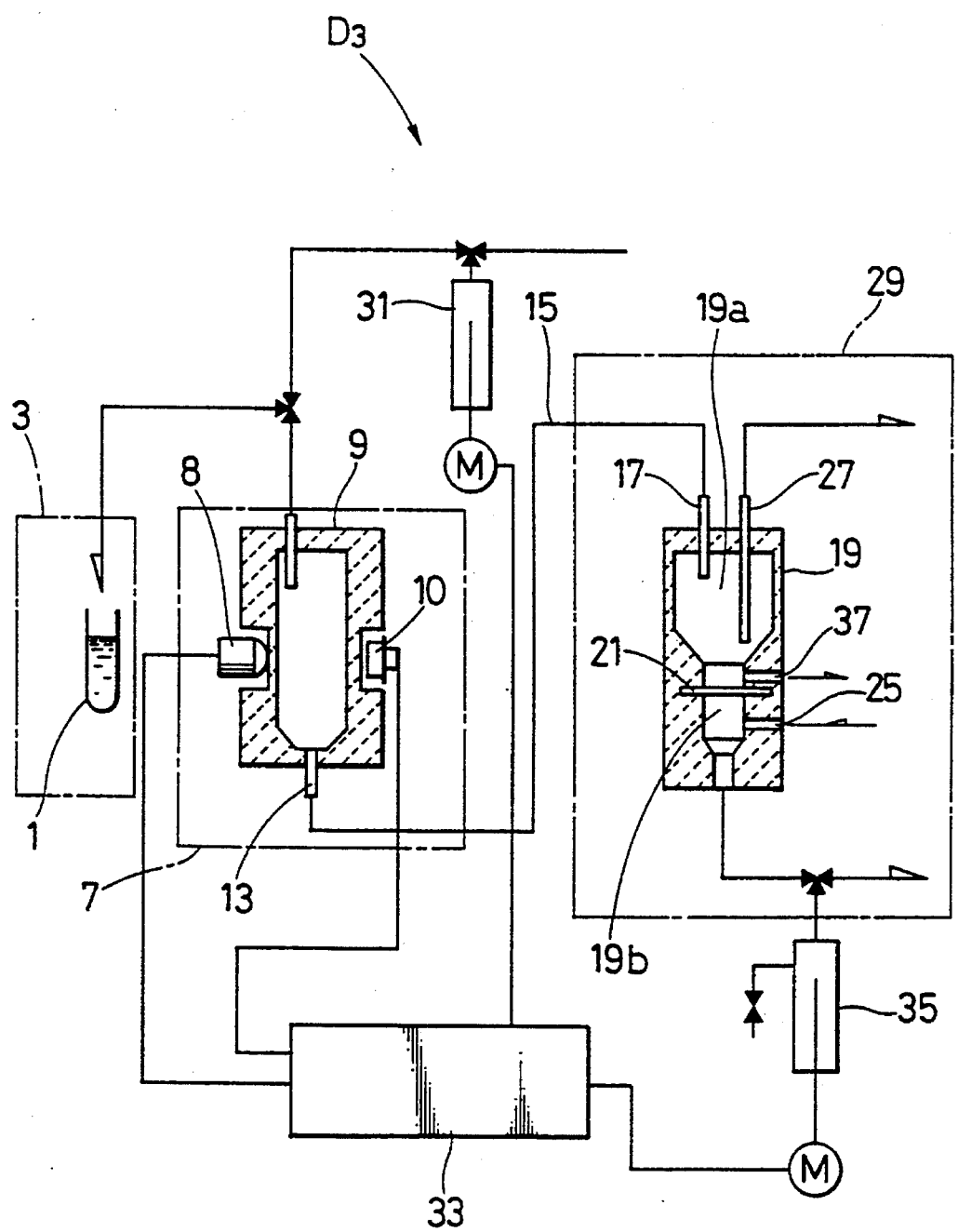
FIG. 6 is a block diagram illustration outlining the basic structure of the sample treatment apparatus according to a further embodiment 3 of the present invention.

In FIG. 6 illustrating the embodiment 3 of the present invention, a sample treatment apparatus $D_3$ is provided with a sample concentration detecting section 7 serving as the concentration measurement means and a sample condensing section 29. A sample sucking section 3 is a section for drawing a measuring liquid sample (blood) stored in sample vessel 1. The sample sucking section 3 has a sample sucking syringe 31, which is controlled by a sample concentration controller 33, serving as the control means. A certain amount of sample measured by the syringe 31 is led to the sample concentration detecting section 7.

The sample concentration detecting section 7 is provided with a sample concentration detecting chamber 9, light source 8, and light receiving element 10, and it measures the quantity of light absorbed or scattered by the particle component in the measuring sample by detecting a change of the quantity of light emitted from the light source 8, by the light receiving element 10. Thereafter, the signal detected by the light receiving element 10 is processed by the sample concentration controller 33, and the particle concentration of the sample is generally obtained.

Sample condensing section 29, is provided with sample condensing chamber 19, and filter 21 each of which constitutes a part of a condensation unit. The sample condensing section 29, condenses the sample sent from the sample concentration detecting section 7, to the sample condensing section 29 through a sample discharge port 13, a sample transfer tube 15, and a sample intake port 17. The filter 21 can use various types of flat-membrane filters. However, when considering the adhesiveness of particles to filter 21, it is preferable to use a screen filter of the type in which holes are made to a thin resin film (e.g. Isopore track-etched Membrane Filter made by Millipore Corporation, U.S.A.) or a porous filter like a microchannel plate.

Moreover, chamber 19 is provided with a front chamber 19a into which the sample flows in above the filter 21 and a rear chamber 19b for discharging the liquid component of the sample through filter 21.

The sample concentration controller 33 determines the condensation rate of the sample so that a measuring system can guage the optimum particle concentration in accordance with the particle concentration measured by the sample concentration detecting section 7. In addition, the sample concentration controller 33 controls the operation of the sample sucking syringe 31 and it can also change the drawn quantity for each sample.

A sample condensing syringe 35, serving as the liquid discharge means draws the liquid stored in the sample condensing syringe 19 in accordance with the control signal sent from the sample concentration controller 33. Thus, the sample is condensed by sucking the liquid component of the sample using syringe 35 and capturing the particle component in filter 21.

This embodiment uses a particle measuring method according to nephelometry as a method for previously measuring the particle concentration in a measuring sample by the sample concentration detecting section 7.

The change of the quantity of LED light transmitted into chamber 9 is measured by using, for example, LED as the light source 8, and a photodiode as the light receiving element 10. Then, the particle concentration is decided with the incident light intensity and the received light intensity according to the Lambert-Beer law.

The condensation rate of the sample to be inspected is determined by comparing the measured data with the particle concentration of the standard sample and the syringe 35 is operated according to the condensation rate. In this case, it is also possible to set the comparative particle concentration to a higher value.

Hereafter, a description is made in accordance with a measuring procedure.

For example, in the case where using a standard sample concentration of 2,000 particles/μl and measuring two kinds of specimen of sample concentration of 200 particles/μl (sample A) and of 4,000 particles/μl (sample B), it is found that sample A must be condensed 10 times and sample B can be measured as it as or measured by diluting it two times in order to measure them at the reproducibility (random error) almost equal to that of the standard sample.

[The case of measurement of the sample A]

Sample A drawn by the sample sucking section 3 (the sucking amount of the sample A is assumed to be 10 ml) is injected into chamber 9 of the sample concentration detecting section 7 and the transmitted light intensity ($I_tA$) of sample A is measured under the incident light intensity $I_o$. The measured result is compared with the transmitted light intensity ($I_tS$) of the standard sample by the sample concentration controller 33. In this case, if the transmitted light intensity $I_tA$ of the sample A equals 1.26 $I_tS$, the expression "$C\epsilon=\log(I_tA/I_tS)=\log(1.26\ I_tS/I_tS)=\log 1.26$" is obtained from the above expression "$C\epsilon=\log(I_o/I_t)$". That is, it is found that the particle concentration of the sample A is approx. 1/10 (=log 1.26) of the particle concentration of the standard sample.

The measured sample is transferred from the sample intake port 17 of the sample condensing section 29 to the sample condensing cheer 19 through the sample discharge port 13 and the sample transfer tube 15. In chamber 19, syringe 35 operates in accordance with the signal sent from the sample concentration controller 33 and the sample in the chamber 19 is condensed 10 times by drawing 9 ml of the liquid component.

Thereafter, the particle component attached to the surface of the filter 21 is removed from the back surface of the filter 21 by a method of "feeding a very small amount of cleaning liquid or a very small number of bubbles from a cleaning liquid (diluent liquid) intake port 25 to filter 21 through the syringe 35 (in this case, the syringe 35 functions as a liquid feed means)". Moreover, in this case, it is possible to use the application of agitating and homogenizing the sample in the chamber 19. Furthermore, it is possible to feed the previously discharged liquid component instead of "feeding the cleaning liquid".

The sample (1 ml) condensed to the optimum concentration for a counter is transferred to an analyzer (not illustrated) through a condensed sample discharge port 27. Thereafter, the cleaning liquid drawn by the sample sucking syringe 31, is sent into the sample concentration detecting section 7 to clean the sample detecting chamber 9 and transferred from the sample intake port 17 of the sample condensing section 29, to the sample condensing chamber 19 through sample discharge port 13 and tube 15. Then, the cleaning liquid washes chamber 19 and is then discharged from a sample discharge port 37. In addition, it is possible to remove residual bubbles from the bottom of filter 21 of chamber 19 by inversely feeding a proper amount of cleaning liquid from syringe 35.

[The case of measurement of the sample B]

Approximating the previous case, sample B is sucked by the sample sucking section 3 (the sucked amount of the sample B is assumed 10 ml) and is then injected into sample concentration detecting section 7. The transmitted light intensity ($I_tB$) is measured under the incident light intensity $I_o$. The measured result is compared with the transmitted light intensity ($I_tS$) of the standard sample by the sample concentration controller 33. In this case, if the transmitted light intensity $I_tB$ of the sample B equals 0.01 $I_tS$, the expression "$C\epsilon=\log(I_tB/I_tS)=\log(0.01\ I_tS/I_tS)=\log 0.01$" is obtained from the above expression "$C\epsilon=\log(I_o/I_t)$". That is, it is found that the particle concentration of the sample B is approx. two times (=log 0.01) larger than the particle concentration of the standard sample.

In this case, because the measurement may be performed with the particle concentration as it is, the measured sample is transferred from sample intake port 17 of the sample condensing section 29, to chamber 19 through the sample discharge port 13 and the tube 15 and thereafter directly transferred to the counter through the condensed sample discharge port 27. Similar to the case of sample A, chambers 9 and 19 are washed.

When measuring a sample with a higher particle concentration, a phenomenon occurs that where particle measurement accuracy decreases due to the simultaneous passage or adjacent passage of particles at a time of measurement when the particle concentration increases. To prevent the acuracy of measurement from decreasing due to the aforementioned phenomenon, it is also possible to dilute the sample up to a proper particle concentration by introducing a diluent liquid from syringe 35 to chamber 19 in accordance with the result measured by sample concentration detecting section 7.

As described above, the measurement of particles at the most reliable range of a measuring apparatus is derived by first roughly measuring the particle concentration of the sample to be inspected by a method such as nephelometry and condensing (or diluting) the sample in accordance with the measured result.

Moreover, the method has the advantage that the detection ability of a cell which has a low appearance frequency, and cannot be detected by the normal measuring method, can be improved by condensing the sample.

Embodiment 4

Figure 7:
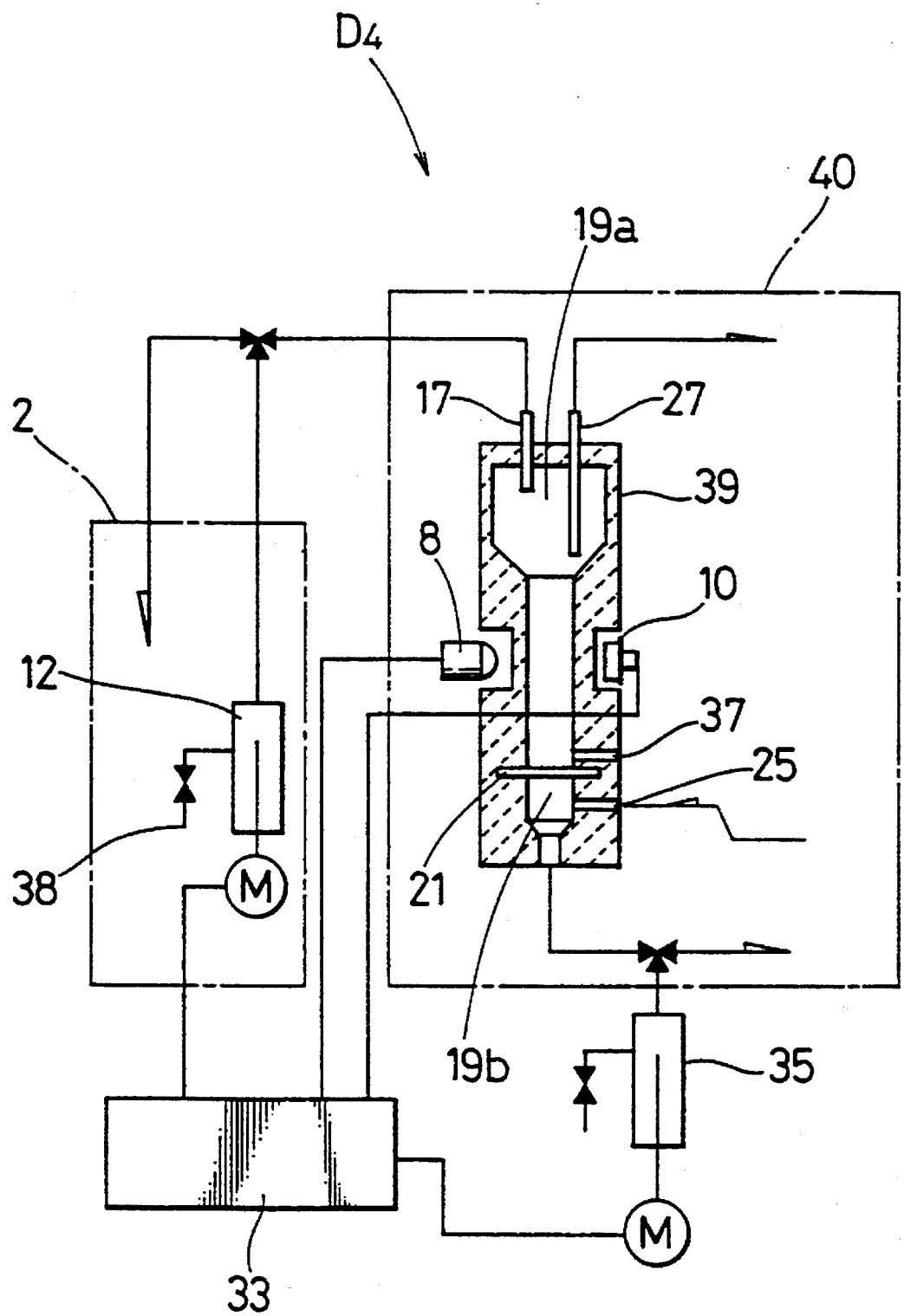
FIG. 7 is a block diagram illustration indicating the basic structure of the sample treatment apparatus according to a still further embodiment 4 of the present invention.

In FIG. 7 which illustrates the embodiment 4 of the present invention, a sample treatment apparatus $D_4$ is provided with the sample sucking section 2, a sample concentration detecting and condensing section 40. The sample concentration detecting and condensing section 40, is constituted by integrating the sample concentration detecting section (concentration measurement means) and the sample condensing section of the embodiment 1. That is, the sample treatment apparatus $D_4$ measures the sample concentration in a sample condensing cheer 39 serving as the condensation unit and performs the condensing operation. Cheer 39 is provided with a front cheer 39a into which the sample flows in above filter 21 and a rear chamber 39b for discharging the liquid component of the sample under filter 21.

Because the sample treatment apparatus $D_4$ has less transfer sections as compared with the embodiment 1, the remaining sample in the channel is lower. It has the advantage that the channel can be easily washed. Moreover, the above method makes it possible to condense a sample while measuring the sample concentration in real time because the concentration measurement means and the condensation unit are set in the same chamber 39. As a result, it is possible to condense a sample with any concentration up to the optimum concentration and improve the measurement accuracy (reproducibility).

Furthermore, because the sample drawing quantity of the sample sucking syringe 12 and that of the sample condensing syringe 35 are accurately controlled by the sample concentration controller 33, it is possible to accurately calculate the concentration of the original sample liquid from the sample sucking quantities of two kinds of syringes, 12 and 35. This occurence is similar with the other embodiments.

What is claimed is:

1. A sample treatment apparatus comprising:
   concentration measurement means for measuring the concentration of an object particle component contained in a liquid sample;
   a concentration adjustment unit for adjusting the concentration of the particle component of the sample to a predetermined value, said concentration adjustment unit being connected to an outlet of the concentration measurement means and including a front chamber having a sample intake port and a discharge port, a rear chamber having a liquid component discharge port, and a filter set so as to separate both chambers from each other and capable of passing the liquid component of the sample without passing the particle component of the sample;
   discharge means, connected to the rear chamber discharge port of the concentration adjustment unit, for discharging a first portion of the liquid component from the front chamber to the rear chamber and for discharging the remaining portion of the sample from the front chamber discharge port to outside of the concentration adjustment unit; and
   control means for operating the discharge means responsive to said concentration measurement means and thereby controlling the concentration of the remaining portion of the sample discharged from the front chamber discharge port in accordance with the measured results by the concentration measurement means.

2. A sample treatment apparatus according to claim 1, wherein the liquid sample is humor which is blood, lymph or urine containing particle components which are particulates, microorganisms or organic cells.

3. A sample treatment apparatus according to claim 1, wherein the discharge means is provided with a syringe and a selector valve.

4. A sample treatment apparatus according to claim 1, wherein the control means determines the amount of the liquid component to be discharged by the discharge means in accordance with the concentration of the particle component obtained by the concentration measurement means and controls the operation of the discharge means.

5. A sample treatment apparatus according to claim 1, wherein a single unit serves as both said concentration measurement means and said concentration adjustment unit.

6. A sample treatment apparatus according to claim 1, wherein a liquid feed means which is connected to the rear chamber of the concentration adjustment unit and feeds a liquid which is diluent liquid or cleaning liquid to the rear chamber is further provided, and
   the control means further regulates the concentration measurement means and the liquid feed means.

7. A sample treatment apparatus according to claim 6, wherein the liquid feed means is provided with a syringe and a selector valve.

8. A sample treatment apparatus according to claim 1, wherein the concentration measurement means includes a chamber for storing the liquid sample, a light source, a light receiving element, and wherein the change of the quantity of light emitted from the light source passing through the sample in the chamber is detected by the light receiving element to obtain the concentration of the particle component.

9. A sample treatment apparatus according to claim 8 which is further provided with dye feed means, connected to the chamber of the concentration measurement means, for feeding a dye to be applied to the sample in the chamber.

10. A sample treatment apparatus according to claim 9, wherein said dye feed means is provided with a syringe and a selector valve.

11. A sample treatment apparatus according to claim 1, wherein the concentration adjustment unit is a condensation unit for condensing the sample by discharging the first portion of the liquid component of the sample entered into the front chamber from the rear chamber through the filter by the discharge means, thereby capturing the particle component of the sample by use of the filter.

12. A sample treatment apparatus according to claim 11 which is further provided with a feed channel connected to the discharge port of the front chamber of the condensation unit and which feeds said remaining portion of the sample to a particle analyzer serving as an analyzing system.

13. A sample treatment apparatus according to claim 12, wherein said particle analyzer is a flow cytometer.

* * * * *